United States Patent
Ishizawa et al.

(10) Patent No.: US 7,425,303 B2
(45) Date of Patent: Sep. 16, 2008

(54) AUTOMATIC ANALYZER

(75) Inventors: Masato Ishizawa, Hitachinaka (JP);
Yohichi Aruga, Hitachinaka (JP);
Kazumi Kusano, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 736 days.

(21) Appl. No.: 10/716,468

(22) Filed: Nov. 20, 2003

(65) Prior Publication Data
US 2004/0101440 A1 May 27, 2004

(30) Foreign Application Priority Data
Nov. 21, 2002 (JP) ............................ 2002-337352

(51) Int. Cl.
*G01N 21/00* (2006.01)
(52) U.S. Cl. ............................ 422/63; 422/64; 422/65; 422/99; 422/100; 422/101; 436/180; 73/19.1
(58) Field of Classification Search ........... 422/99–101, 422/63–65; 73/19.1; 436/180
See application file for complete search history.

(56) References Cited

U.S. PATENT DOCUMENTS 5,319,954 A * 6/1994 Koeda et al. ................. 73/19.1

* cited by examiner

*Primary Examiner*—Jill Warden
*Assistant Examiner*—Jyoti Nagpaul
(74) *Attorney, Agent, or Firm*—Mattingly, Stanger, Malur & Brundidge, P.C.

(57) ABSTRACT

Disclosed is an automatic analyzer that includes a reagent vessel for containing a reagent, a pipette probe that has a liquid surface detection function and dispenses a reagent from the reagent vessel, a reaction vessel for containing a reagent that is dispensed from the pipette probe, an analysis mechanism for measuring a reaction between a reagent and a sample within the reaction vessel, a storage means for memorizing liquid surface position information that is acquired by the liquid surface detection function, a liquid surface estimation mechanism for estimating the current liquid surface position in accordance with time-sequential changes in liquid surface information stored by the storage means, and a function for controlling a dispensing operation of the pipette probe in accordance with the result of liquid surface estimation by the liquid surface estimation mechanism.

19 Claims, 4 Drawing Sheets

AUTOMATIC ANALYZER

BACKGROUND OF THE INVENTION

The present invention relates to an automatic analyzer that automatically makes qualitative/quantitative analyses of blood, urine, and other biological samples, and more particularly to an automatic analyzer that incorporates a function for dispensing a liquid from one vessel to another with a pipette probe.

The automatic analyzer dispenses a blood, urine, or other biological sample from its vessel into a reaction vessel, then dispenses a reagent from its vessel into the reaction vessel, which contains the dispensed biological sample, and measures color changes in a mixture of the sample and reagent with a photometer or other measuring means.

When the sample and reagent are to be dispensed, the end of a pipette probe is dipped in the liquid to be dispensed. The greater the dipping depth, the larger the amount of liquid deposited on the outer wall of the probe and thus the greater the degree of contamination between different samples and reagents. A method generally employed for minimizing the pipette probe dipping depth is to stop the descent of the probe when its end is positioned slightly below the liquid surface after the surface of the contained liquid is detected, and then exercise operational control so as to suction a specified amount of liquid for transfer to the probe. In this instance, a technology for accurate liquid surface detection is essential. Various technologies have been proposed to achieve the above purpose, including a method for measuring changes in the capacitance between a pipette probe and liquid and a method for measuring changes in the pressure within a pipette probe.

While a sample or reagent is being dispensed, the surrounding air may be taken in so as to bubble on the liquid surface. In such an instance, a capacitance measurement method (which makes use of a significant capacitance change that occurs when a pipette probe comes into contact with a liquid) may erroneously conclude that the liquid surface is reached when the pipette probe comes into contact with the bubble surface, thereby making it impossible to dispense a specified amount of reagent or sample. The automatic analyzer disclosed by Japanese Patent Laid-Open No. Hei 148207 incorporates a function for turning off a liquid surface detection circuit so as not to erroneously recognize a bubble as the liquid surface and includes means for calculating the pipette probe descent position necessary for minimizing the contact between a reagent or other liquid in a reaction tube and the pipette probe for sample dispensing in accordance with the amount of reagent or other liquid discharged beforehand into the reaction tube, and stopping the descent of the pipette probe in compliance with the calculated value.

Some reagents contain constituents that readily deposit as well as a surface-active agent that is likely to bubble. To obtain consistent analysis results from the use of one of such reagents, it is necessary to periodically stir it during the analyzer's analysis operation for the purpose of making the reagent concentration uniform within a reagent vessel. Therefore, the reagent surface bubbles after such a stirring operation. After the stirring operation is repeated a certain number of times, a layer of bubbles may be formed on the reagent liquid surface.

As a result, when an attempt is made to detect the reagent liquid surface within the reagent vessel, the layer of bubbles may be erroneously detected instead of the true reagent liquid surface so as to start a dispensing operation before the end of the probe reaches the liquid surface. In other words, reagent bubbles may be dispensed instead of the reagent liquid so that an inadequate amount of reagent is dispensed. Eventually, an analysis result error may occur.

The technology disclosed by Patent Document 1 above uses the amount of a reagent or other liquid discharged into a reaction tube to calculate the surface of the reagent or other liquid in the reaction tube. However, this technology cannot calculate the reagent liquid surface if the surface of a reagent liquid initially contained in a reagent vessel is bubbled.

SUMMARY OF THE INVENTION

It is therefore an object of the present invention to provide an automatic analyzer that comprises means for detecting the liquid surface even when the reagent liquid contained in a reagent vessel is bubbled.

The surface of a reagent in a reagent vessel is not usually bubbled immediately after the reagent vessel is set in an automatic analyzer. Subsequently, however, the reagent is periodically stirred during the automatic analyzer's analysis operation for the purpose of making the reagent concentration uniform within a reagent vessel. Bubble formation occurs upon each periodic stirring so that the liquid surface detection operation becomes erratic. To achieve the above-mentioned object, the present invention provides an automatic analyzer that is capable of memorizing liquid surface height changes that are encountered when dispensing is conducted with a limited number of stirring operations, extrapolating the subsequent liquid surface height changes, and estimating the current liquid surface even when it is bubbled.

BRIEF DESCRIPTION OF THE DRAWINGS

Other objects and advantages of the invention will become apparent from the following description of embodiments with reference to the accompanying drawings in which.

DETAILED DESCRIPTION OF THE PREFERRED EMBODIMENTS

Embodiments of the present invention will now be described with reference to the accompanying drawings beginning with FIG. 1.

Figure 1:
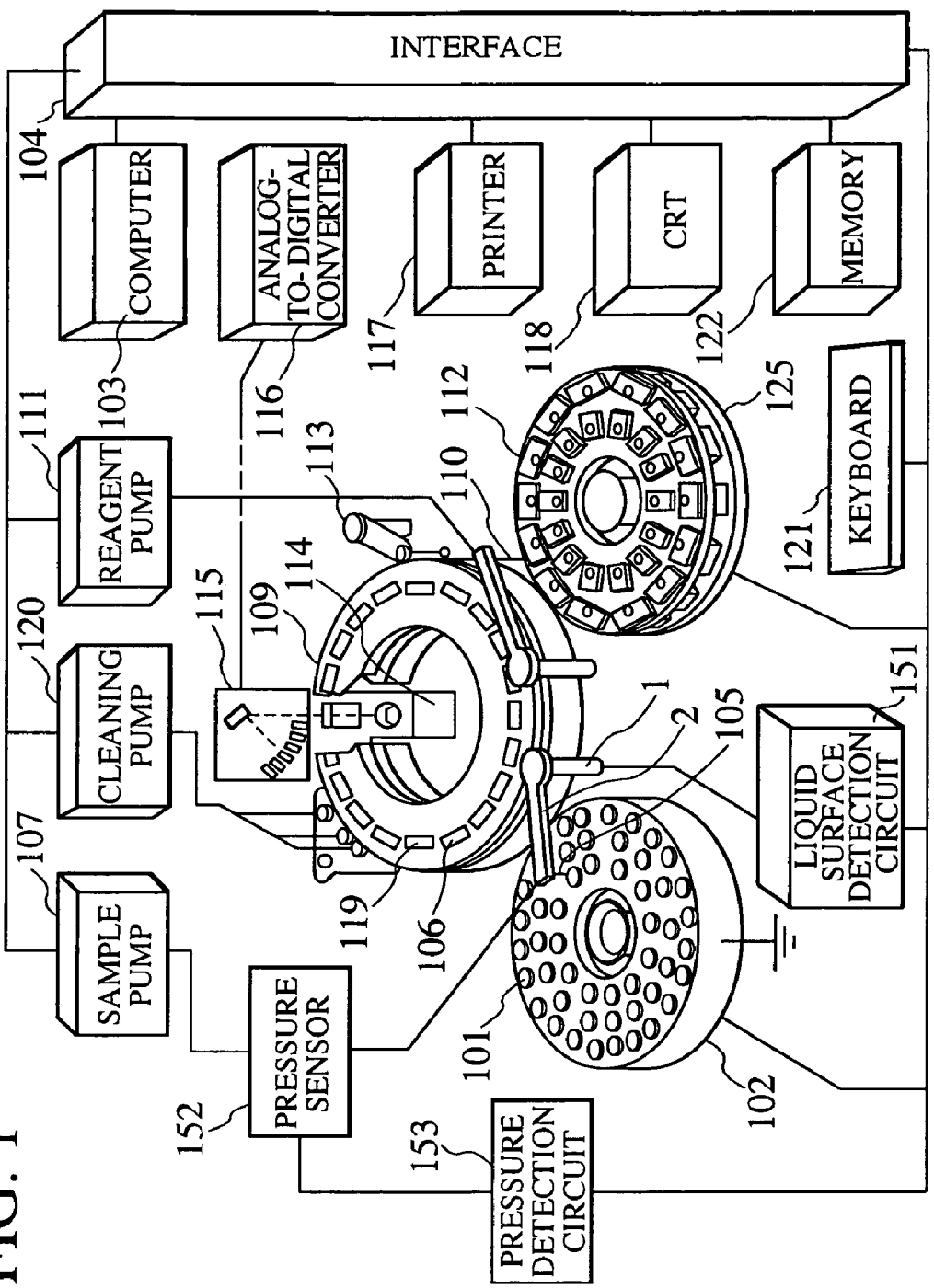
FIG. 1 is a schematic diagram illustrating the overall configuration of an automatic analyzer to which the present invention is applied.

FIG. 1 is a schematic diagram illustrating the dispensing mechanism of a general automatic analyzer. Since the functions of the components shown in the figure are well known in the art, they are described in detail herein. A sampling arm 2 of a sampling mechanism 1 not only moves up and down but also rotates. The sampling arm 2 uses a probe 105, which is mounted on the sampling arm 2, suctions a sample 7 in a sample vessel 101 that is mounted on a sample disc 102, which rotates clockwise and counterclockwise, and then discharges the suctioned sample into a reaction vessel 106. As is obvious from the figure, a commonly employed structure permits universal layout in which the sample vessel 101 can be directly mounted on the sample disc 102 or mounted on a test tube (not shown).

The structure of the automatic analyzer shown in FIG. 1 will be continuously described. Reagent bottles 112 corresponding to a plurality of analyses to be made are arranged on a reagent disc 125, which freely rotates. A reagent pipette probe 110, which is mounted on a movable arm, dispenses a specified amount of reagent from a reagent bottle 112 to the reaction vessel 106.

A sample pipette probe 105 performs a sample suction/discharge operation in accordance with the operation of a sample syringe pump 107. The reagent pipette probe 110 performs a reagent suction/discharge operation in accordance with the operation of a reagent syringe pump 111. A keyboard 121, a screen on a CRT 118, or some other input device is used to enter analysis items to be analyzed for a sample. A computer 103 controls all component unit operations of the automatic analyzer.

When the sample disc 102 intermittently rotates, the sample vessel 101 is transferred to a sample suction position. The sample pipette probe 105 descends to enter the sample vessel while it is halted. When the end of the descending pipette probe 105 comes into contact with the liquid surface of the sample, a liquid surface detection circuit 151 generates a detection signal. When such a detection signal is generated, the computer 103 exercises control to stop the descent of the drive section for a movable arm 2. Next, the pipette probe 105 takes in a specified amount of sample by the force of suction, and then ascends to the top dead center. While the pipette probe 105 suctions a specified amount of sample, a pressure detection circuit 153 uses a signal from a pressure sensor 152 to monitor internal pressure changes within a flow path between the pipette probe 105 and sample syringe pump 107. If any abnormal pressure change is found during suctioning, the pressure detection circuit 153 attaches an alarm to the affected analysis data because it is highly probable that the specified amount of sample is not suctioned.

Next, the sampling arm 2 swivels horizontally, lowers the sample pipette probe 105 at a position of the reaction vessel 106 on a reaction disc 109, and discharges the retained sample into the reaction vessel 106. When the reaction vessel 106, which contains the sample, moves to a reagent adding position, a reagent associated with a target analysis item is added from the reagent pipette probe 110. In accordance with sample and reagent dispensation, the liquid surfaces of the sample in the sample vessel 101 and the reagent in the reagent bottle 112 are detected. An agitator 113 stirs a mixture in the reaction vessel to which the sample and reagent are added. While a row of reaction vessels move, a plurality of reaction vessels block a beam of light emitted from a light source 114 so that a photometer 115, which is provided as a measuring mean, measures the absorbance or luminescence value of each mixture. An absorbance signal is derived from measurement and entered into the computer 103 via an analog-to-digital converter 116 and an interface 104. The computer 103 calculates the concentration of the analysis item. The result of analysis is printed onto a printer 117 via the interface 104 or displayed on the CRT 118. Further, the analysis result is stored on a hard disk 122, which serves as a memory. After completion of photometry, the reaction vessel 106 is cleaned at a position of a cleaning mechanism 119. A cleaning pump 120 not only supplies cleaning water to the reaction vessel, but also discharges waste from the reaction vessel. In an example shown in FIG. 1, three rows of vessel retainers are formulated so that three rows of sample vessels 101 can be set concentrically on the sample disc 102, and one sample suctioning position is set for each row in order to permit the sample pipette probe 105 to suction the sample.

Figure 2:
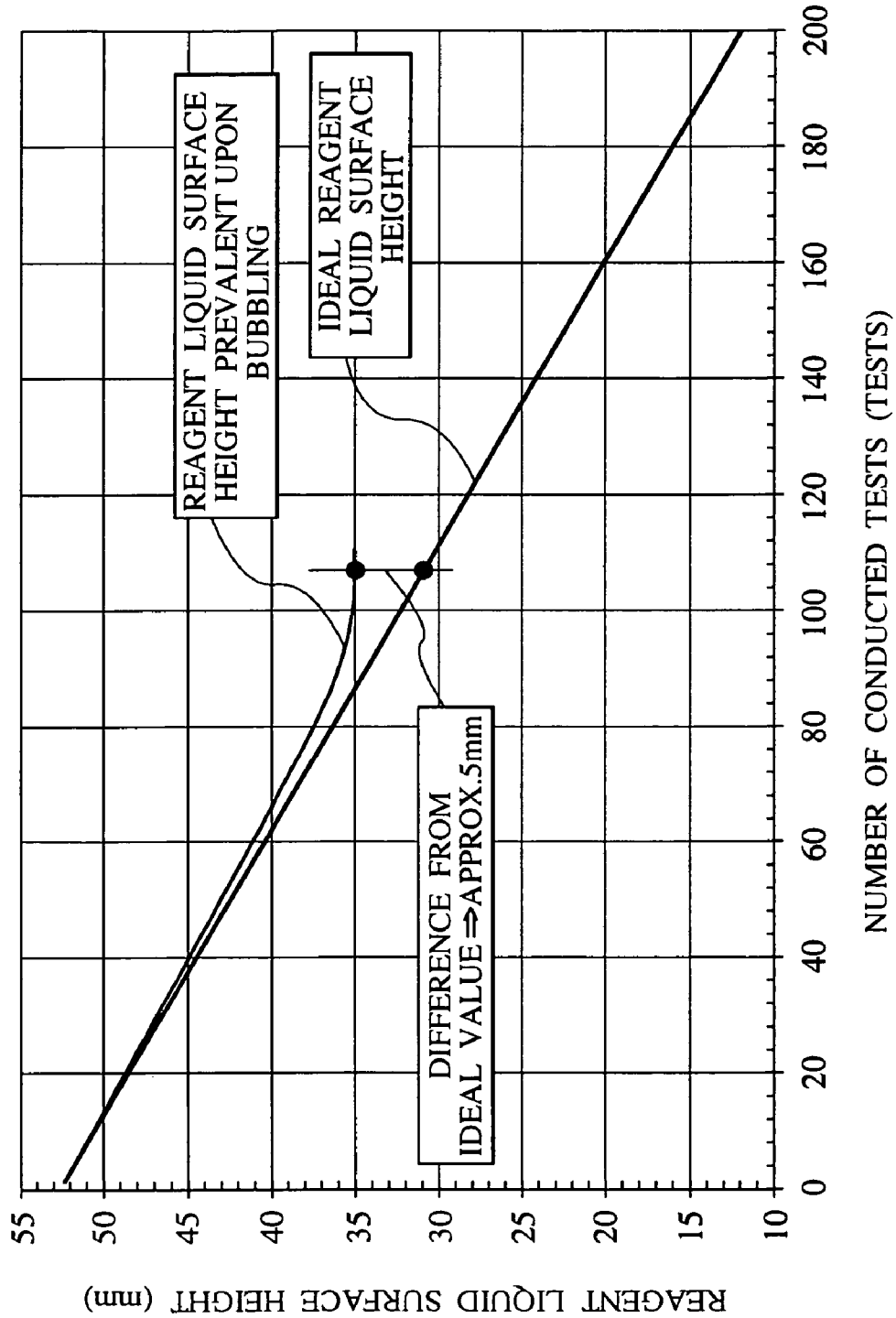
FIG. 2 indicates how the reagent liquid surface height changes upon bubbling and how the ideal-reagent liquid surface height changes.

An adverse effect of air bubbles generated within a reagent vessel will now be described with reference to FIG. 2. As described earlier, some reagents contain constituents that readily deposit as well as a surface-active agent that is likely to bubble. To obtain consistent analysis results from the use of one of such reagents, it is necessary to periodically stir it during the analyzer's analysis operation for the purpose of making the reagent concentration uniform within a reagent vessel. Although the liquid surface within the reagent vessel is eventually detected for suctioning after a stirring operation, the reagent liquid surface is bubbled due to stirring. After the stirring operation is repeated a certain number of times, a layer of bubbles may be formed on the reagent liquid surface. In FIG. 2, the "Reagent liquid surface height prevalent upon bubbling" curve indicates reagent liquid surface level changes. As indicated in FIG. 2, bubble formation occurs on the reagent liquid surface due to stirring as the number of conducted tests increases. Finally, a layer of bubbles, which is several centimeters in thickness, is formed. However, when liquid surface detection occurs, the pipette probe is dipped in the reagent liquid to a level slightly below the liquid surface for the purpose of avoiding contamination. More specifically, control is exercised so as to stop the pipette probe's descent when the end of the pipette probe is dipped to a depth of approximately 2 to 4 mm and then suction a specified amount of liquid for transfer into the pipette probe.

Therefore, if, due to reagent liquid bubbling, a difference of several millimeters, more specifically, approximately 5 mm or greater exists between the "Ideal reagent liquid surface height", that is, the true liquid surface height, and the "Reagent liquid surface height prevalent upon bubbling" as indicated in FIG. 2, the above-mentioned reagent dipping depth for a liquid surface detection operation is not adequate for reaching the true liquid surface. Thus, the reagent liquid is not suctioned from the true liquid surface, and the reagent bubbles formed on the true liquid surface are dispensed. Eventually, an analysis result error may occur.

Figure 3:
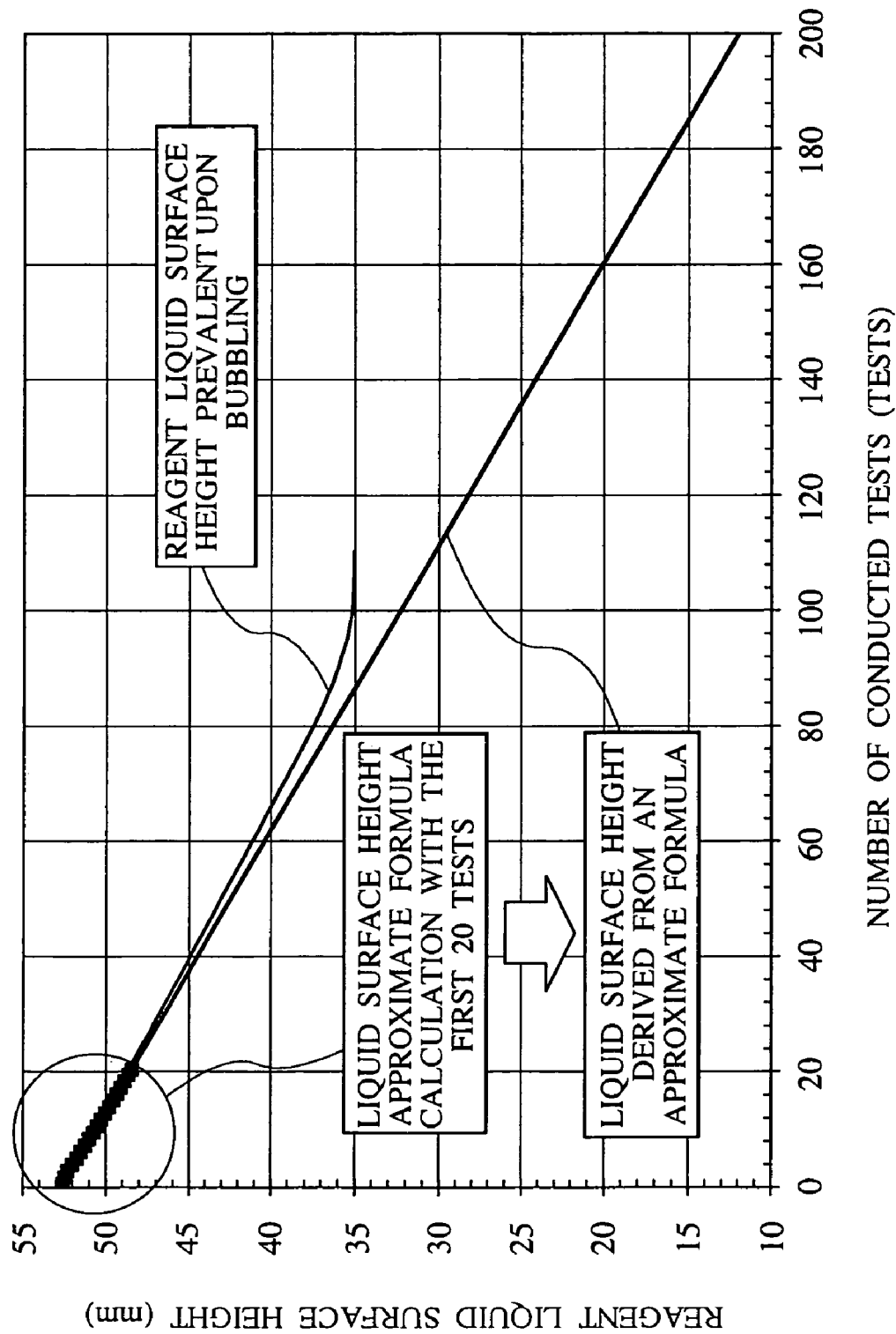
FIG. 3 indicates changes in the reagent liquid surface height according to the present invention.

One embodiment of the present invention will now be described with reference to FIGS. 2 and 3. As described above, the difference between the "Ideal reagent liquid surface height", that is, the true liquid surface height, and the "Reagent liquid surface height prevalent upon bubbling" increases with an increase in the number of conducted tests. However, when the number of conducted tests is approximately 40, that is, when a stirring operation has been repeated a small number of times, the degree of bubble formation is insignificant so that no apparent liquid surface height difference exists. The present invention makes use of ideal liquid surface height changes that occur during a period of the first several tens of tests for analysis during which no significant bubble formation occurs, and estimates the reagent liquid surface height, which varies with a subsequent increase in the number of conducted tests, from the liquid surface height changes with the above period. An example shown in FIG. 3 indicates the "Reagent liquid surface height prevalent upon bubbling" curve and "Liquid surface height derived from an approximate formula" curve, which are obtained when an approximate formula is prepared according to the least-squares method and by using the liquid surface height changes encountered during the first 20 tests for analysis. As is obvious from FIG. 3, the "Liquid surface height derived from an approximate formula" curve is equivalent to the "Ideal reagent liquid surface height" shown in FIG. 2. It can be said that the "Liquid surface height derived from an approximate formula" curve in FIG. 3 represents changes in the true liquid surface height. For example, true liquid surface height changes calculated from the approximate formula can be monitored as an expected value during an analysis operation. In an expected liquid surface height detection operation, the pipette probe is further lowered by a specific amount from the liquid surface height expected from the bubbles on the reagent until the expected liquid surface is reached and without stopping even if a liquid surface detection signal is entered early. Further, the pipette probe is dipped several millimeters deep into the reagent. In this manner, the pipette probe can pass through the bubble layer without fail, reach the liquid surface properly, and dispense a specific amount of reagent.

In the above example, an approximate curve is drawn by the least-squares method to calculate the "Liquid surface height derived from an approximate formula". However, the least-squares method need not always be used. Alternatively, the approximate formula may be prepared in accordance with a gradient that is calculated from the reagent liquid surface differences derived from the tests. The present invention does not have to dictate a specific method for approximate formula calculation.

Next, the above-mentioned true liquid surface position is further adjusted by an ideal method to obtained an optimum value. A plurality of means will now be described with reference to FIG. 4.

It is conceivable that the accuracy of calculation with the approximate formula may be lowered, for instance, by the following factors:

(1) Abnormal liquid surface height change data among the data targeted for approximate curve calculation (2) Carryover of reagent deposited on the outer circumferential surface of the pipette probe (3) Evaporation of reagent in the reagent bottle Factor (1) will now be described in detail. If any existing data targeted for approximate curve calculation indicates a significant change in the liquid surface height, it may excessively increase or decrease the gradient of the approximate curve. However, if the employed system defines a normal change range or normal data range for targeted data and such a range is exceeded by certain data, such data can be excluded from approximate curve calculation. In this manner, the true liquid surface can be calculated without sacrificing the approximate curve accuracy.

Figure 4:
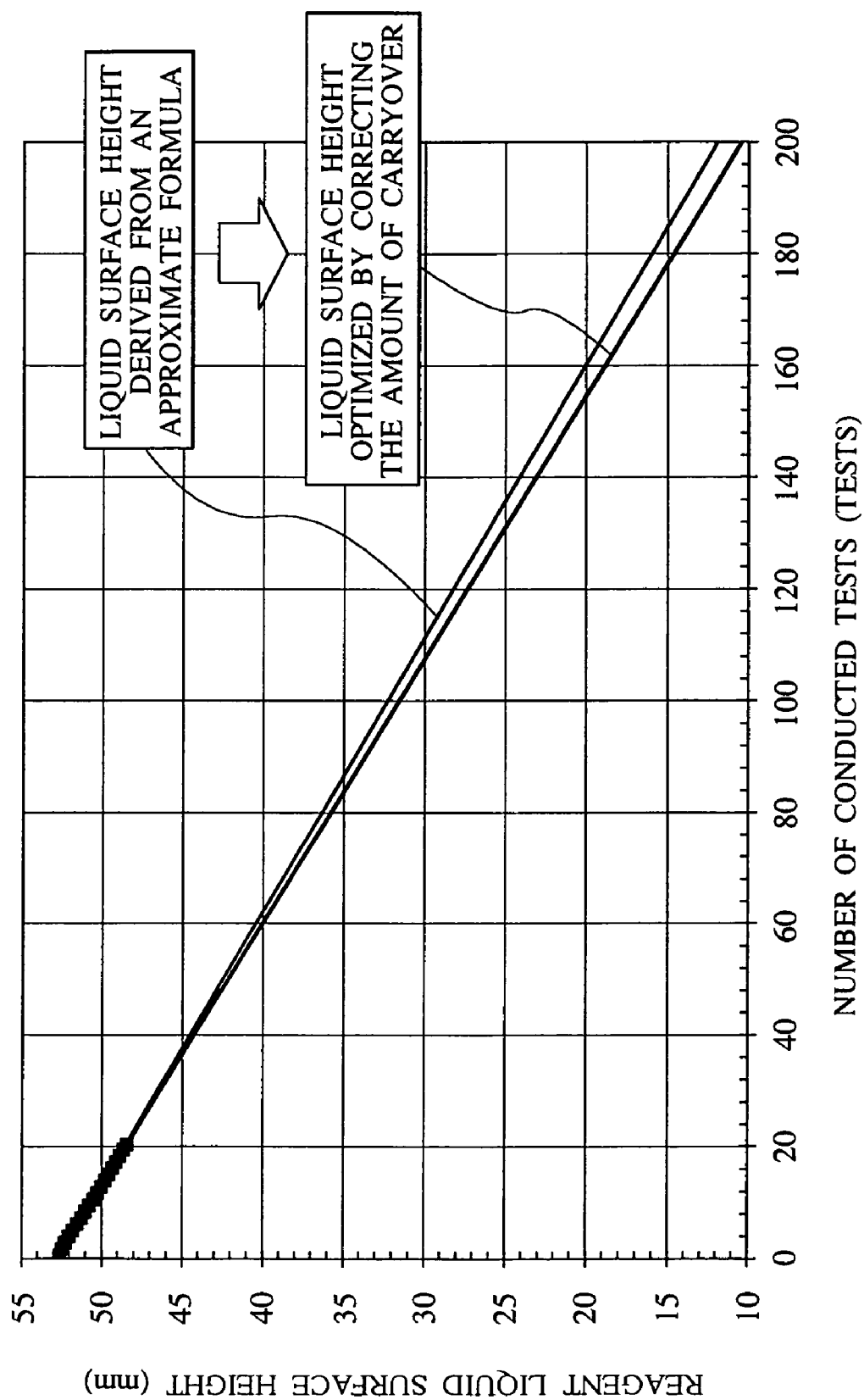
FIG. 4 indicates changes in the reagent liquid surface height according to the present invention and optimized changes in the reagent liquid surface height.

Factor (2) will now be described in detail. The "Liquid surface height derived from an approximate formula", which is calculated as indicated in FIG. 4, is an expected value. However, if the pipette probe is dipped into the bubble layer formed by a stirring operation and the liquid is suctioned from the true liquid surface position, it can easily be imagined that the carryover remaining on the outer circumferential surface of the pipette probe (the amount of reagent that is left on the outer circumferential surface of the pipette probe, carried over, and lost due to cleaning by a probe cleaning mechanism) would greatly increase when compared with a period of the first several tens of tests for analysis targeted for approximate formula calculation, and that the resulting position would be lower than the liquid surface position calculated according to the approximate formula. Therefore, the true liquid surface height can easily be optimized, as indicated by the "Liquid surface height optimized by correcting the amount of carry-over" curve shown in FIG. 4, by correcting the expected liquid surface height by subtracting the amount of carryover from the "Liquid surface height derived from an approximate formula" curve shown in FIG. 4. The appropriate correction value for use would be approximately 5 µl per suctioning operation. As a matter of course, the amount of carryover increases or decreases in proportion to the bubble layer height. However, the system can estimate whether bubbles are generated and estimate the layer height from the expected value, which is derived from the "Liquid surface height derived from an approximate formula", and from the liquid surface height detected when such a liquid surface height is prevalent. Therefore, it is easy to create a configuration that optimizes the amount of carryover, which is proportional to the bubble layer height.

Factor (3) will now be described in detail. If any existing data targeted for approximate curve calculation indicates an evaporation-induced, abnormal decrease in the detected liquid surface height, it may excessively increase or decrease the gradient of the approximate curve. In this instance, too, the system can conduct a monitoring operation during a time interval between the last liquid surface detection and the current liquid surface detection for the purpose of judging whether liquid surface detection has not been accomplished for a long period of time during which evaporation may occur or a period of several weeks or judging whether the above data has arisen unexpectedly. If the data is recognized as the data representing an evaporation-dependent difference that has arisen after long standing, the approximate curve can be calculated without lowering the approximate curve accuracy even in the event of evaporation by decrementing all the previously collected approximate formula minimum data until they match the subsequently detected liquid surface changes and acquiring the resulting data as the data targeted for the approximate formula. If the data has arisen unexpectedly, on the other hand, the approximate curve accuracy can be maintained by excluding it from calculation as is the case with factor (1).

Further, in the first liquid surface detection operation performed after the liquid surface has not been detected for a long period of time, it can be estimated, even if evaporation occurs after approximate curve calculation, that no bubbles exist as a matter of course, and that the liquid surface position is reliable. Therefore, the true liquid surface, as mentioned earlier, can easily be followed by correcting the approximate formula so as to match subsequently detected changes in the liquid surface height.

In another embodiment, the expected value derived from the above-mentioned "Liquid surface height derived from an approximate formula" is compared against the liquid surface position determined by liquid surface detection upon each detection. If an unduly high liquid surface position is detected due, for instance, to abnormal bubble formation, it is conceivable that the reagent is not uniform due to the use of an abnormal paddle for stirring. If the detected liquid surface position is unduly lower than expected due to considerable evaporation, it is conceivable that the concentration is abnormal due to a concentrated reagent. In these situations, abnormal data may be generated as analysis results. Therefore, it is easy to establish a system that automatically issues an alarm to prevent abnormal data from being reported.

As is obvious from the foregoing embodiments, the true liquid surface position can be calculated with high accuracy by a method for estimating the remaining liquid surface height that can be expected from liquid surface height changes encountered upon liquid surface detection, that is, the method for calculating the true liquid surface height with an approximate formula after absorbing individual differences involving physical variations, for instance, in syringe pump suction volume accuracy, reagent bottle forming error, and reagent disc levelness error. It is therefore easy to construct a high-reliability apparatus because various applied functions can be implemented to provide means for locating an apparatus abnormality with ease by letting the system monitor the expected liquid surface position. If the estimated liquid surface height differs from the liquid surface height measured by the pipette probe, it is conceivable that bubbles may be generated. In this instance, the range of reagent deposits on the outer circumferential surface of the pipette probe is increased by the bubble height. Such reagent deposits may incur reagent contamination. Therefore, if such a condition is detected, a desired effect may be achieved by enlarging the range of normal reagent pipette probe cleaning. As such being the case, better results can be obtained by creating a program that enlarges the reagent pipette probe cleaning range when the difference between the estimated liquid surface height and measured liquid surface height is greater than predefined.

As described above, if the surface of a reagent liquid contained in a reagent vessel is bubbled or covered with a layer of bubbles, the bubble layer is detected instead of the true reagent liquid surface so that the end of the reagent pipette probe starts a dispensing operation before it reaches the liquid surface. In other words, reagent bubbles are dispensed instead of the reagent liquid so that an analysis result error may eventually occur. However, the present invention provides an automatic analyzer that causes the reagent pipette probe to reach the reagent liquid surface even when the reagent is covered with a layer of bubble, suctions the expected amount of reagent properly, and produces consistent analysis results.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. An automatic analyzer, including:
   a reagent vessel for containing a reagent;
   a pipette probe that has a liquid surface detection function and dispenses a reagent from said reagent vessel;
   a reaction vessel for containing a reagent that is dispensed from said pipette probe;
   an analysis mechanism for measuring a reaction between a reagent and a sample within said reaction vessel;
   a storage means for memorizing liquid surface position information that is acquired by said liquid surface detection function;
   a liquid surface estimation mechanism for estimating the current liquid surface height derived from an approximate formula curve based on liquid surface height changes that occur during a period of the first several tens of tests for analysis; and
   a controller for controlling a dispensing operation of said pipette probe in accordance with the result of liquid surface estimation by said liquid surface estimation mechanism,
   further comprising a mechanism for automatically adjusting the liquid surface estimation result estimated by said liquid surface estimation mechanism based on an amount of a carryover that remains on the outer circumferential surface of said pipette probe.

2. The automatic analyzer according to claim 1, further comprising an agitation mechanism for stirring a reagent within said reagent vessel.

3. The automatic analyzer according to claim 2, wherein said approximate formula is prepared according to the least-squares method.

4. The automatic analyzer according to claim 3, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

5. The automatic analyzer according to claim 2, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

6. The automatic analyzer according to claim 1, wherein said approximate formula is prepared according to the least-squares method.

7. The automatic analyzer according to claim 6, further comprising a mechanism for automatically adjusting the liquid surface estimation result estimated by said liquid surface estimation mechanism based on an amount of reagent evaporation from a reagent vessel.

8. The automatic analyzer according to claim 7, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

9. The automatic analyzer according to claim 6, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

10. The automatic analyzer according to claim 1, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

11. The automatic analyzer according to claim 1, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

12. An automatic analyzer, including:
    a reagent vessel for containing a reagent;
    a pipette probe that has a liquid surface detection function and dispenses a reagent from said reagent vessel;
    a reaction vessel for containing a reagent that is dispensed from said pipette probe;
    an analysis mechanism for measuring a reaction between a reagent and a sample within said reaction vessel;
    a storage means for memorizing liquid surface position information that is acquired by said liquid surface detection function;
    a liquid surface estimation mechanism for estimating the current liquid surface height derived from an approximate formula curve based on liquid surface height changes that occur during a period of the first several tens of tests for analysis; and
    a controller for controlling a dispensing operation of said pipette probe in accordance with the result of liquid surface estimation by said liquid surface estimation mechanism, further comprising a mechanism for automatically adjusting the liquid surface estimation result estimated by said liquid surface estimation mechanism based on an amount of reagent evaporation from a reagent vessel.

13. The automatic analyzer according to claim 12, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

14. An automatic analyzer, including:
a reagent vessel for containing a reagent;
a pipette probe that has a liquid surface detection function and dispenses a reagent from said reagent vessel;
a reaction vessel for containing a reagent that is dispensed from said pipette probe;
an analysis mechanism for measuring a reaction between a reagent and a sample within said reaction vessel;
a storage means for memorizing liquid surface position information that is acquired by said liquid surface detection function;
a liquid surface estimation mechanism for estimating the current liquid surface height derived from an approximate formula curve based on liquid surface height changes that occur during a period of the first several tens of tests for analysis; and
a controller for controlling a dispensing operation of said pipette probe in accordance with the result of liquid surface estimation by said liquid surface estimation mechanism,
further comprising an agitation mechanism for stirring a reagent within said reagent vessel; and
a mechanism for automatically adjusting the liquid surface estimation result estimated by said liquid surface estimation mechanism based on an amount of a carryover that remains on the outer circumferential surface of said pipette probe.

15. The automatic analyzer according to claim 14, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

16. An automatic analyzer, including:
a reagent vessel for containing a reagent;
a pipette probe that has a liquid surface detection function and dispenses a reagent from said reagent vessel;
a reaction vessel for containing a reagent that is dispensed from said pipette probe;
an analysis mechanism for measuring a reaction between a reagent and a sample within said reaction vessel;
a storage means for memorizing liquid surface position information that is acquired by said liquid surface detection function;
a liquid surface estimation mechanism for estimating the current liquid surface height derived from an approximate formula curve based on liquid surface height changes that occur during a period of the first several tens of tests for analysis; and
a controller for controlling a dispensing operation of said pipette probe in accordance with the result of liquid surface estimation by said liquid surface estimation mechanism,
wherein said approximate formula is prepared according to the least-squares method,
further comprising a mechanism for automatically adjusting the liquid surface estimation result estimated by said liquid surface estimation mechanism based on an amount of a carryover that remains on the outer circumferential surface of said pipette probe.

17. The automatic analyzer according to claim 16, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

18. An automatic analyzer, including:
a reagent vessel for containing a reagent;
a pipette probe that has a liquid surface detection function and dispenses a reagent from said reagent vessel;
a reaction vessel for containing a reagent that is dispensed from said pipette probe;
an analysis mechanism for measuring a reaction between a reagent and a sample within said reaction vessel;
a storage means for memorizing liquid surface position information that is acquired by said liquid surface detection function;
a liquid surface estimation mechanism for estimating the current liquid surface height derived from an approximate formula curve based on liquid surface height changes that occur during a period of the first several tens of tests for analysis; and
a controller for controlling a dispensing operation of said pipette probe in accordance with the result of liquid surface estimation by said liquid surface estimation mechanism,
further comprising an agitation mechanism for stirring a reagent within said reagent vessel; and
a mechanism for automatically adjusting the liquid surface estimation result estimated by said liquid surface estimation mechanism based on an amount of reagent evaporation from a reagent vessel.

19. The automatic analyzer according to claim 18, further comprising a mechanism for cleaning a pipette probe more extensively during dispensing than in a normal dispensing operation if a difference greater than predefined exists between the liquid surface height estimated by said liquid surface estimation mechanism and the liquid surface height measured by said liquid surface detection function.

* * * * *